US00PP11544P

United States Patent [19]

Olesen et al.

[11] Patent Number: Plant 11,544

[45] Date of Patent: Oct. 3, 2000

[54] MINIATURE ROSE PLANT NAMED 'POULYN'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/122,435

[22] Filed: Jul. 24, 1998

[51] Int. Cl.[7] ..... A01H 5/00

[52] U.S. Cl. ..... Plt./121

[58] Field of Search ..... Plt./116, 121

*Primary Examiner*—Howard J. Locker

[57] ABSTRACT

A new miniature pot rose plant which has abundant, dark pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE DISCOVERY

The present discovery constitutes a new and distinct variety of a miniature rose plant which was discovered in a cultivated area. The mutation resulted from 'POULnye', a patented variety by the same inventors which is described and illustrated in U.S. Plant Pat. No. 8,942 and issued on Oct. 18, 1994. The new rose variety resulted from a naturally occuring mutation of unknown causation on a branch of 'POULnye' which was discovered in a controlled planting.

The rose plant of the present discovery has a unique combination of characteristics which are outstanding in the new variety and which distinguish it from the orginal rose 'POULnye' as well as all other varieties which we are aware of. For example, the new variety has:

1. Abundant dark pink flowers;
2. Vigorous and compact growth;
3. Year-round flowering under glasshouse conditions;
4. Suitability for production from softwood cuttings in pots;
5. Durable flowers and foliage which make the variety suitable for distribution in the floral industry.

This combination of qualities is not present in previously available commercial cultivars of this type and distinguish 'POULyn' from all other varieties of which we are aware.

The resulting mutation was selected and evaluations were conducted of the resulting rose plants in a controlled environment.

Asexual reproduction of 'POULyn' by cuttings was first done by L. Pernille and Mogens N. Olesen in their nursery in Fredensborg, Denmark in April, 1996. This initial and other subsequent propagations have demonstrated that the characteristics of 'POULyn' are true to type and are transmitted from one generation to the next.

BRIEF DESCRIPTION OF THE DRAWING

The accompanying color illustration show as true as is reasonably possible to obtain in color photographs of this type, the typical characteristics of the buds, flowers, leaves, stems, and a plant of 'POULyn'. Specifically illustrated in SHEET 1:

1. Stem and branches showing the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULyn', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, the nearest existing rose variety is 'POULnye', a patented variety described and illustrated in U.S. Plant Pat. No. 8,942 and issued on Oct. 18, 1994. Chart 1 details several physical characteristics of 'POULyn' and 'POULnye'.

CHART 1

| | 'POULyn' | 'POULnye' |
|---|---|---|
| Bud Color | Red-Purple Group 62A | Red-Purple Group 62C |
| Bloom color, upon opening | Red-Purple Group 63A. | Red-Purple Group 62B |
| Bloom color, after opening | Red-Purple Group 63B. | Red-Purple Group 62C |
| Basal petal spot | Green-White Group 157C | Yellow Group 4D |

Mutation of: 'POULnye'.

Classification:

*Botanical.*—*Rosa hybrida.*

*Commercial.*—Miniature.

FLOWER AND FLOWER BUD

Blooming habit: Continuous.

Flower bud:

*Size.*—14–16 mm in length when petals are just beginning to crack open, from base of receptacle to tip of bud.

*Bud form.*—Pointed to pointed ovoid.

*Bud color.*—Red-Purple Color 42A Group at ¼ opening.

*Sepals.*—Green Group 137A. Weak to moderate foliaceous appendages on three of the five sepals. Surfaces of remaining sepals slightly pubescent. Very limited number of stipitate glands present on margins of sepals with appendages.

*Peduncle.*—Moderate number of stipitate glands present. Length: 40–50 mm average length. Color: Green Group 143B. Prickles: None observed.

*Receptacle.*—Surface: Smooth. Shape: Broadly urn-shaped. Size: Small. 4 mm×4 mm. Color: Yellow-Green Group 143B.

*Borne.*—Several together, with average three to five buds per flowering stem.

Flower bloom:

*Size.*—Medium for a 10 cm pot rose. 30–35 mm diameter on average.

*Form.*—Shape of flower when viewed from the side: Upon opening, upper part: Flattened convex. Upon opening, lower part: Convex. Open flower, upper part: Flattened convex. Open flower, lower part: Flat. Petals are reflexed when fully open.

*Petalage.*—Double. Average range: 30–40 under normal conditions.

*Color.*—Upon opening, the upper surface of the petals is Red-Purple Group 63A. Upon openng, the reverse side is Red-Purple Group 62A. After opening, the upper surface is Red-Purple Group 63B. After opening, the reverse surface is Red-Purple Group 62A. Upon opening, a petal spot of Green-White Group 157C exists on the inner and outer sides of the bases of the innermost petals. Upon opening, a petal spot Green-White Group 157C exists on the inner and outer bases of the outermost petals.

*Petal margin.*—Center of petal margin is pointed.

*Petaloids.*—Small petaloids present. Quantities 10–15, generally.

*Fragrance.*—Slight.

*Duration.*—As a pot plant, flowers last from 15 to 18 days. As a cut flower 8 to 12 days.

*General tonality.*—Red-Purple Group 63A until flowers are open 3 days. Afterwards, general tonality is Red-Purple Group 63B.

Reproductive organs:

*Pollen.*—Color: Yellow Group 11C. Abundance: Limited or not present.

*Anthers.*—Size: Medium. Few or none present. Color: Yellow Group 11C and Green-White Group 157C.

*Filaments.*—Few or none present.

*Stigmas.*—Superior in location to anthers. Color: Yellow-Green Group 149C.

*Styles.*—Color: Yellow-Green Group 149C.

PLANT

Plant growth: Vigorous, compact, and upright to bushy pot rose. When grown as a 10 cm pot plant, the average height of the plant itself is 16–18 cm and the average width is 18–20 cm. When grown as a nursery plant on its own roots the average plant height is 25–35 cm and the average plant width is 25–30 cm.

Stems:

*Color.*—Young wood: Green Group 143C. Older wood: Green Group 143C.

*Prickles.*—Incidence: Few. Size: Average length: 3–4 mm. Color: Upper portion of the stem: Orange-White Group 159C. Lower portion of the stem: Greyed-Orange Group 165D. Shape: Straight.

*Bark.*—Young wood: Smooth. Older wood: Smooth.

Plant foliage: Normal number of leaflets on normal leaves in middle of stem: 5 leaflets.

*Leaf size.*—Small. 70 (l) mm×35 (w) mm.

*Abundance.*—Above average.

*Color.*—Upper Leaf Surface: Green Group 137A. Lower Leaf Surface: Green Group 138B. Juvenile foliage: Green Group 137C to 138B. Serrations with slight intonation of Greyed-Red Group 179A.

Plant leaves and leaflets:

*Stipules.*—Present. Color: Green Group 137B. Size: 7–9 mm in length. Hairs: Few or none.

*Petiole.*—Length: 12–15 mm. Color: Green-Group 137B. Underneath: Without prickles. Upper edge of petiole rachis with stipitate glands.

*Leaflet edge.*—Finely serrated.

*Shape.*—Leaflets are pointed ovate.

*Leaflets.*—Number: 5.

*Other.*—Moderately glossy, thick texture.

Disease resistance: Above average resistance to black spot and mildew under normal greenhouse growing conditions.

We claim:

1. A new and distinct variety of rose plant of the miniature class, substantially as herein illustrated and described as a distinct and novel rose variety due to its abundant dark pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

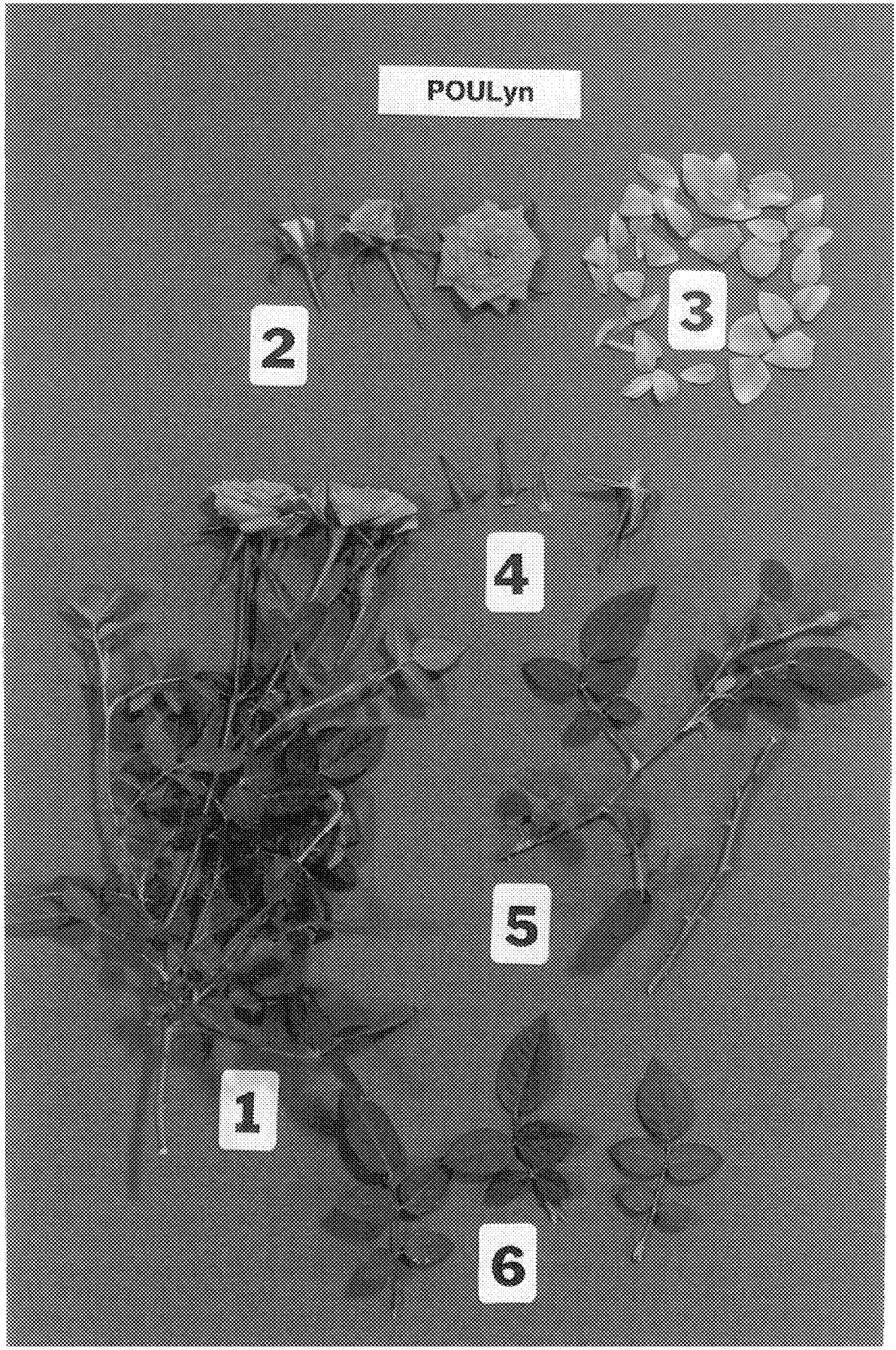
POULyn
2
3
4
5
1
6